United States Patent
Chein (10) Patent No.: US 6,187,750 B1
(45) Date of Patent: Feb. 13, 2001

(54) METHOD OF HORMONE TREATMENT FOR PATIENTS WITH SYMPTOMS CONSISTENT WITH MULTIPLE SCLEROSIS

(75) Inventor: Edmund Y. M. Chein, Beverly Hills, CA (US)

(73) Assignee: Everyoung Technologies, Inc., Palm Springs, CA (US)

(*) Notice: Under 35 U.S.C. 154(b), the term of this patent shall be extended for 0 days.

(21) Appl. No.: 09/385,133

(22) Filed: Aug. 25, 1999

(51) Int. Cl.[7] .................................................. A61K 38/27
(52) U.S. Cl. .............................. 514/12; 514/21; 514/171; 514/177; 514/178; 514/182; 514/415; 514/903; 424/580; 424/586
(58) Field of Search ............................... 514/12, 21, 171, 514/177, 178, 182, 415, 903; 424/580, 586

(56) References Cited

U.S. PATENT DOCUMENTS

| | | | |
|---|---|---|---|
| 4,727,041 | * 2/1988 | Aroonsakul | 436/8 |
| 4,791,099 | 12/1988 | Aroonsakul | 514/171 |
| 4,897,389 | * 1/1990 | Aroonsakul | 514/171 |
| 4,898,856 | 2/1990 | Aroonsakul | 514/171 |
| 4,898,857 | 2/1990 | Aroonsakul | 514/171 |
| 4,902,680 | 2/1990 | Aroonsakul | 514/171 |
| 5,017,470 | 5/1991 | Aroonsakul | 435/4 |
| 5,391,381 | 2/1995 | Wong et al. | 424/473 |
| 5,397,771 | 3/1995 | Bechgaard et al. | 514/2 |
| 5,424,199 | 6/1995 | Goeddel et al. | 435/69.4 |
| 5,434,146 | 7/1995 | Labrie et al. | 514/169 |
| 5,550,107 | 8/1996 | Labrie | 514/11 |
| 5,563,131 | 10/1996 | Berliner et al. | 514/177 |
| 5,691,169 | 11/1997 | Dalbage et al. | 438/69.7 |
| 5,691,325 | * 11/1997 | Sandyk | 514/159 |
| 5,855,920 | * 1/1999 | Chein | 424/568 |

FOREIGN PATENT DOCUMENTS

WO 95/32991    7/1995  (WO).

OTHER PUBLICATIONS

"Administration of Human Somatotropin in Levodopa–Treated Patients With Parkinsonism" by Paul S. Papavasiliou et al., *Arch Neurol*, vol. 36, Oct. 1979.

"Long–Term Influence of Levodopa on Bone Mass and Growth Hormone in Postmenopausal Women with Parkinson's Disease" by H. Rico, et al., *Clinical Neuropharmacology*, vol. 10, No. 1, pp. 87–91, 1987.

"Clinical Studies of the Cholinergic Deficit in Alzheimer's Disease" by Bonnie M. Davis, MD, et al., *Journal of the American Geriatrics Society*, vol. 33, No. 11.

"Disturbances of Pituitary Function in Central Nervous System Disease" by Glenn T. Peake, MD, et al., *Medical Clinics of North America*, vol. 52, No. 2, Mar. 1968.

"Growth Hormone Response in Parkinson's Disease" by J.D. Parkes, et al., *The Lancet*, Feb. 28, 1976.

"Blood Levels of FSH, LH, TSH, And GH in Parkinsonian patients Before and During L–Dopa Treatment" by P.O. Lundberg, *Acta Neurol. Scandinav.*, vol. 48, pp. 427–432, 1972.

"Therapeutic Approaches in Parkinson's Disease: Possible Roles of Growth Hormone and Somatostatin" by George C. Cotzias, et al., *The Basal Ganglia*, 1976.

"Effects of Estrogen, Progestin and Combined Estrogen–Progestin Oral Contraceptive Preparations on Experimental Allergic Encephalomyelitis" by Barry G. Arnason et al., Boston, MA.

"Molecular Biology of Neurological and Psychiatric Disorders. I. Effect of Parkinsonism, Age, Sex, and L–Dopa on Platelet Monoamine Oxidase" by E.A. Zeller, et al., *Journal of Neutral Transmission*, 39, pp. 63–77, 1976.

"Peliosis Hepatis Report of Nine Cases" by Tsutomu Karasawa, et al., *Acta Path. Jap.*, 29(3), pp. 457–469, 1979.

"Orale Ovulationshemmer—Indikationen und Komplikationen aus Neurologischer Sicht" by Sigrid Poser, *Fortschr. Neurol. Psychiat.*, 45, 1977.

"Contraccezione Orale e Sclerosi Multipla" by A. Ghezzi, et al., *Archivio per le Scienze Mediche*, 136, 1979.

"Estrogens and Extrapyramidal System" by P. Bedard, et al., *The Lancet*, Dec. 24 & 31, 1977.

"Etude des Androgenes Plasmatiques Chez les Femmes Atteintes de Maladies Auto–Immunes" by M. Dougados, et al., *Revue du Rhumatisme*, 1984, 51(3), pp. 145–149.

"Observations in a Preliminary Open Trial of Estradiol Therapy for Senile Dementia–Alzheimer's Type" by Howard Fillit, et al., *Psychoneuroendocrinology*, vol. 11, No. 3, pp. 337–345, 1986.

"Metabolic Effects of GH: A Rationale for Continued GH Treatment of GH–Deficient Adults After Cessation of Linear Growth" by A. Juul, et al., Department of Growth and Reproduction, University of Copenhagen, Denmark. *Horm Res* (Switzerland) 1995, 44 Suppl 3, pp. 64–72, ISSN 0301–0163, Journal Code GBI.

"Insulin–Like Growth Factor I Alters Peripheral Thyroid Hormone Metabolism in Humans: Comparison with Growth Hormone" by M.A. Hussain, et al., Division of Endocrinology and Metabolism, University Hospital of Zurich, Switzerland. *Eur J Endocrinol* (Norway) May 1996, 134(5) pp. 563–7, ISSN 0804–4643, Journal Code BXU.

"Improved Final Height in Girls with Turner's Syndrome Treated with Growth Hormone and Oxandrolone" by K.O. Nilsson, et al., Department of Pediatrics, University Hospital Malmo, Sweden. *J Clin Endocrinol Metab* (United States) Feb. 1996, 81(2) pp. 635–40, ISSN 0021–972X, Journal Code HRB.

(List continued on next page.)

Primary Examiner—F. T. Moezie
(74) *Attorney, Agent, or Firm*—Blakely Sokoloff Taylor & Zafman LLP (57) ABSTRACT

A method for treating patients having symptoms consistent with multiple sclerosis comprising administering a regimen of doses of human growth hormone of less than 0.5 mg/day. In one aspect, the method includes replenishing one or more of melatonin, thymus, thyroid, adrenal and sex hormones to predetermined levels in conjunction with the human growth hormone.

9 Claims, 9 Drawing Sheets

OTHER PUBLICATIONS

"Insulin, Insulin–Like Growth Factor–Binding Protein–1, and Sex Hormone–Binding Globulin in Patients with Turner's Syndrome: Course Over Age in Untreated Patients and Effect of Therapy with Growth Hormone Alone and in Combination with Oxandrolene"0 by G. Haeusler, et al., Pediatric Department, University of Vienna, Austria. *J Clin Endocrinol Metab* (United States) Feb. 1996, 81(2) pp. 536–41, ISSN 0021–972X, Journal Code HRB.

"Growth Hormone Deficiency in Adults: Characteristics and Response to Growth Hormone Replacement" by S.A. Lieberman, et al., Department of Internal Medicine, University of Texas Medical Branch, Galveston, 77555–1060, USA. *J Pediatr* (United States) May 1996, 128 (5 Pt 2) pp. S58–60, ISSN 0022–3476, Journal Code JLZ.

"Effect of Anabolic Hormones and Insulin–Like Growth Factor–I on Muscle Mass and Strength in Elderly Persons" by W.J. Carter, et al., Memorial Veterans Hospital, Little Rock, Arkansas, USA. *Clin Geriatr Med* (United States) Nov. 1996, 11(4) p. 735–48, ISSN 0749–0690, Journal Code CLN.

"Screening for PIT1 Abnormality by PCR Direct Sequencing Method" by Y. Irie, et al., Department of Laboratory Medicine, Osaka University Medical School, Japan. *Thyroid* (United States) Jun. 1995, 5(3) pp. 207–11, ISSN 1050–7256, Journal Code BJW.

"Trophic Factor Supplementation: Effect on the Age–Associated Changes in Body Composition" by R.S. Schwartz, et al., Division of Gerontology and Geriatric Medicine, Harborview Medical Center, Seattle, USA. *J Gerontol A Biol Sci Med Sci* (United States) Nov. 1995, 50 Spec No. pp. 151–6, ISSN 1079–5006, Journal Code CBA.

"Treatment of Growth Hormone–Deficient Adults with Recombinant Human Growth Hormones Increases the Concentration of Growth Hormone in the Cerebrospinal Fluid and Affects Neurotransmitters" by J.O. Johansson, et al., Department of Internal Medicine, University of Goteborg, Sweden. *Neuroendocrinology* (Switzerland) Jan. 1995, 61(1) pp. 57–66, ISSN 0028–3835, Journal Code NY8.

"Adult Growth Hormone Deficiency" by J.O. Jorgensen, et al., Medical Department M (Endocrinology and Diabetes), Aarhus Kommunehospital, Denmark. *Horm Res* (Switzerland) 1994, 42(4–5) pp. 235–41, ISSN 0301—0163, Journal Code GBI.

"Effects of Recombinant Human Growth Hormone on Metabolic Indices, Bodycomposition, and Bone Turnover in Health Elderly Women" by L. Holloway, et al., Aging Study Unit, Palo Alto Veterans Affairs Medical Center, California 94304. *J Clin Endocrinol Metab* (United States) Aug. 1994, 79(2) pp. 470–9, ISSN 0021–972X, Journal Code HRB.

"Treatment of Growth Delay in Boys With Isolated Growth Hormone Deficiency" by A. Albanese, et al., Medical Unit, Institute of Child Health, London, UK. *Eur J Endocrinol* (Norway) Jan. 1994, 130(1) pp. 65–9, ISSN 0804–4643, Journal Code BXU.

"Management of the Short Stature Due to Pubertal Delay in Boys" by L. Adan, et al., Pediatric Endocrinology Unit, Hopital et Faculte Necker—Enfants Malades, Paris, France. *J Clin Endocrinol Metab* (United States) Feb. 1994, 78(2) pp. 478–82, ISSN 0021–972X, Journal Code HRB.

"Aging and Growth Hormone" by K.K. Ho, et al., Garvan Institute of Medical Research, St. Vincent's Hospital, Sydney, Australia. *Horm Res* (Switzerland) 1993, 40(1–3) pp. 80–6, ISSN 0301–0163, Journal Code GBI.

"Treatment of Adults with Growth Hormone (GH) Deficiency with Recombinant Human GH" by B.A. Bengtsson, et al., Department of Medicine, Sahlgrenska Hospital, Medical Faculty, University of Goteborg, Sweden. *J Clin Endocrinol Metab* (United States) Feb. 1993, 76(2) pp. 309–17, ISSN 0021–972X, Journal Code HRB.

"Regulation of Growth Hormone Binding Protein in Man: Comparison of Gel Chromatography and Immunoprecipitation Methods" by K.K. Ho, et al., Garvan Institute of Medical Research, St. Vincent's Hospital, Sydney, Australia. *J Clin Endocrinol Metab* (United States) Feb. 1993, 76(2) pp. 302–8, ISSN 0021–972X, Journal Code HRB.

"Growth Hormone Therapy in Turner's Syndrome. Impact of Injection Frequency and Initial Bone Age" by C. Rongen–Westerlaken, et al., Department of Pediatrics, University of Utrecht, The Netherlands, *Am J Dis Child* (United States) Jul. 1992, 146(7) pp. 817–20, ISSN 0002–922X, Journal Code 3GS.

"Nocturnal Thyrotropin Surge in Growth Hormone–Deficient Children" by G. Municchi, et al., Developmental Endocrinology Branch, National Institute of Child Health and Human Development, National Institutes of Health, Bethesda, Maryland 20892. *J Pediatr* (United States) Aug. 1992, 121(2) pp. 214–20, ISSN 0022–3476, Journal Code JLZ.

"Effects of Human Growth Hormone in Men Over 60 Years Old" by Daniel Rudman, MD, et al., *The New England Journal of Medicine,* Jul. 5, 1990, vol. 323, No. 1.

"Restoring Ebbing Hormones May Slow Aging" by Jane E. Brody, *The New York Times,* Jul. 18, 1995.

"Life Extension Interview" *Life Extension,* Nov. 1996, pp. 21–27.

"Brave Montel: How I'm Gonna Beat MS" by John Blosser, *National Enquirer,* Sep. 7, 1999.

"Multiple Sclerosis: The Immune System's Terrible Mistake" by Oeter Riskind, MD, PhD, *The Harvard Mahoney Neuroscience Institute Letter, On The Brain,* Fall 1996, vol. 5, No. 4.

"Evaluation of Progression in Multiple Sclerosis by Magnetic Resonance Imaging (MRI)", *National Institute of Neurological Disorders and Stroke (NINDS).*

"Growth Factors and Myelin Regeneration in Multiple Sclerosis" by HD Webster, *Mult Scler,* Apr. 1997; 3(2); pp. 113–20.

"Insulin–Like Growth Factor I Treatment Reduces Clinical Deficits and Lesion Severity in Acute Demyelinating Experimental Autoimmune Encephalomyelitis" by X. Liu, et al., *Mult Scler,* Apr. 1995, 1(1), pp. 2–9.

"Chronic relapsing Experimental Autoimmune Encephalomyelitis: Effects of Insulin–Like Growth Factor–I Treatment on Clinical Deficits, Lesion Severity, Glial Responses, and Blood Brain Barrier Defects" by W. Li, et al., *J Neuropathol Exp Neurol,* May 1998, 57(5), pp. 426–38.

"Insulin–Like Growth Factor–I Treatment Reduces Immune Cell Responses in Acute Non–Demyelinative Experimental Autoimmune Encephalomyelitis" by X. Liu, *J Neurosci Res,* Mar. 1997, 47(5), pp. 531–8.

"Insulin–Like Growth Factor–I Given Subcutaneously Reduces Clinical Deficits, Decreases Lesion Severity and Up–Regulates Synthesis of Myelin Proteins in Experimental Autoimmune Encephalomyelitis" by DL Yao, *Life Sci,* 1996, 58(16), pp. 1301–6.

"Insulin–Like Growth Factor–I Treatment Reduces Demyelination and Up–Regulates Gene Expression of Myelin–Related Proteins in Experimental Autoimmune Encephalomyelitis" by DL Yao, *Proc Natl Acad Sci USA,* Jun. 20, 1995, 92(13), pp. 6190–4.

"A 48–Week (24–Week Baseline Followed by a 24–Week Treatment) Phase II Pilot Study of the Tolerability and Effect/Efficacy of Subcutaneously Administered Insulin–Like Growth Factor–I (rhIGF) (CEP–151) in Multiple Sclerosis (MS) Patients", *National Institute of Neurological Disorders and Stroke (NINDS).*

"Retrospective Analysis of the Effects of Low Dose, High Frequency Human Growth Hormone on Serum Lipids and Prostate Antigen" by Edmund Y. Chein, MD, JD, et al.

*Palm Springs Life Extension Institute Manual,* Dec. 26, 1995.

* cited by examiner

METHOD OF HORMONE TREATMENT FOR PATIENTS WITH SYMPTOMS CONSISTENT WITH MULTIPLE SCLEROSIS

BACKGROUND OF THE INVENTION

1. Field of the Invention

The invention relates to hormone therapy as a treatment for patients with symptoms consistent with multiple sclerosis.

2. Background

It is known that the levels of a variety of hormones drop substantially with age. These include human growth hormone, sex hormones, pineal, adrenal, thyroid, and thymus hormones. Hormonal replenishment methods employed as anti-aging treatments have been developed. An example of such method is described in U.S. Pat. No. 8,855,920. The utility of this method in connection with certain degenerative diseases, often associated with hormonal deficiencies due to aging, is also known in the art.

In contrast, Multiple Sclerosis (MS) is not a disease associated with degenerative conditions associated with old age. Rather, MS strikes mainly young adults and is the most common neurologic cause of disability in that age group. Overall, MS affects approximately 300,000 Americans.

MS is thought to be an autoimmune illness, wherein the immune system mistakenly recognizes normal brain and spinal tissue as "foreign" and attacks them, resulting in inflammation and damage. Myelin, the insulative material surrounding axons in nerve cells, are particularly affected by MS. In patients, the inflammation disrupts myelin, sometimes destroying the axons thus impeding the connections between nerve cells. The region of demyelination and inflammation within the brain or spinal cord is called a "plaque" and ranges anywhere from millimeters to more than a centimeter in diameter.

Actual MS symptoms appear to reflect the number and severity of plaques as well as their location at important sites within the nervous system. Mild sensory symptoms, e.g., tingling, burning, itching, may result. Typically, however, no diagnosis of MS is made until severe symptoms develop, such as weakness, paralysis or numbness of limbs, loss of vision, imbalance, chronic pain or chronic fatigue. The long term consequences of MS can be very debilitating. In some studies, 50% of patients were disabled within ten years and fewer than two thirds were able to walk after thirty years.

In common diagnosis, MS is found by excluding all other potential conditions from consideration. Formerly diagnostic chemical tests of cerebro-spinal fluid determined the presence of MS. This, however, has given way in recent years to magnetic resonance imaging (MRI) scans of the brain as the preferred diagnostic method. Brain MRI scans are abnormal in the vast majority of MS victims. Areas of abnormal brightness, suggesting increased water content, appear on "T2 weighted" scans; dark areas on "T1 weighted" scans suggest focal areas of tissue destruction; and abnormal brightness after a dye is injected for enhancement into the patient's bloodstream suggest that inflammation has damaged the blood-brain barrier. Again, as these symptoms are present also in other neurologic conditions, the diagnosis of MS is not made from these symptoms alone. This diagnosis results by testing done over time.

Various drugs, including natural immune substances such as beta-interferon, have proved effective in treating the physical symptoms of MS and reducing their frequency. Recently studies with animals employing induced experimental autoimmune encephalomyelitis (EAE), an animal model of MS, has shown that growth factor hormones, including Insulin-like Growth Factor hormones (IGF) may promote myelin regeneration, reducing and sometimes eliminating inflammatory lesions and reducing other clinical deficits in EAE subjects. In one study adult female mice having induced EAE were injected subcutaneously with 0.6 mg of IGF over a ten day period. Another group of EAE-induced mice were given placebos. Those treated with IGF-I exhibited reduced deficits and reduced numbers and sizes of inflammatory, demyelinating and demyelinated lesions.

SUMMARY

The invention relates to a hormone replenishment method employed as a treatment for subjects with symptoms consistent with Multiple Sclerosis (MS). The method includes, in one aspect, administering a regimen of human growth hormone (HGH) of less than 0.5 mg per day.

DETAILED DESCRIPTION

The invention relates to a method useful in treating symptoms consistent with MS. In one embodiment, the method includes administering a regimen of doses of HGH of less than 0.5 mg per day. In another embodiment, the method includes determining that the level of human growth hormone and at least two supplemental hormones are below optimal or predetermined physiological levels for an adult human, and establishing a regimen for the replenishment of the level of the deficient hormones to optimal or predetermined physiological levels. The supplemental hormones include the sex hormones, namely testosterone, progesterone, and estrogen, the melatonin hormone, the adrenal hormones, namely DHEA and pregnenolone, the thyroid hormone, and the thymus hormone.

Figure 1:
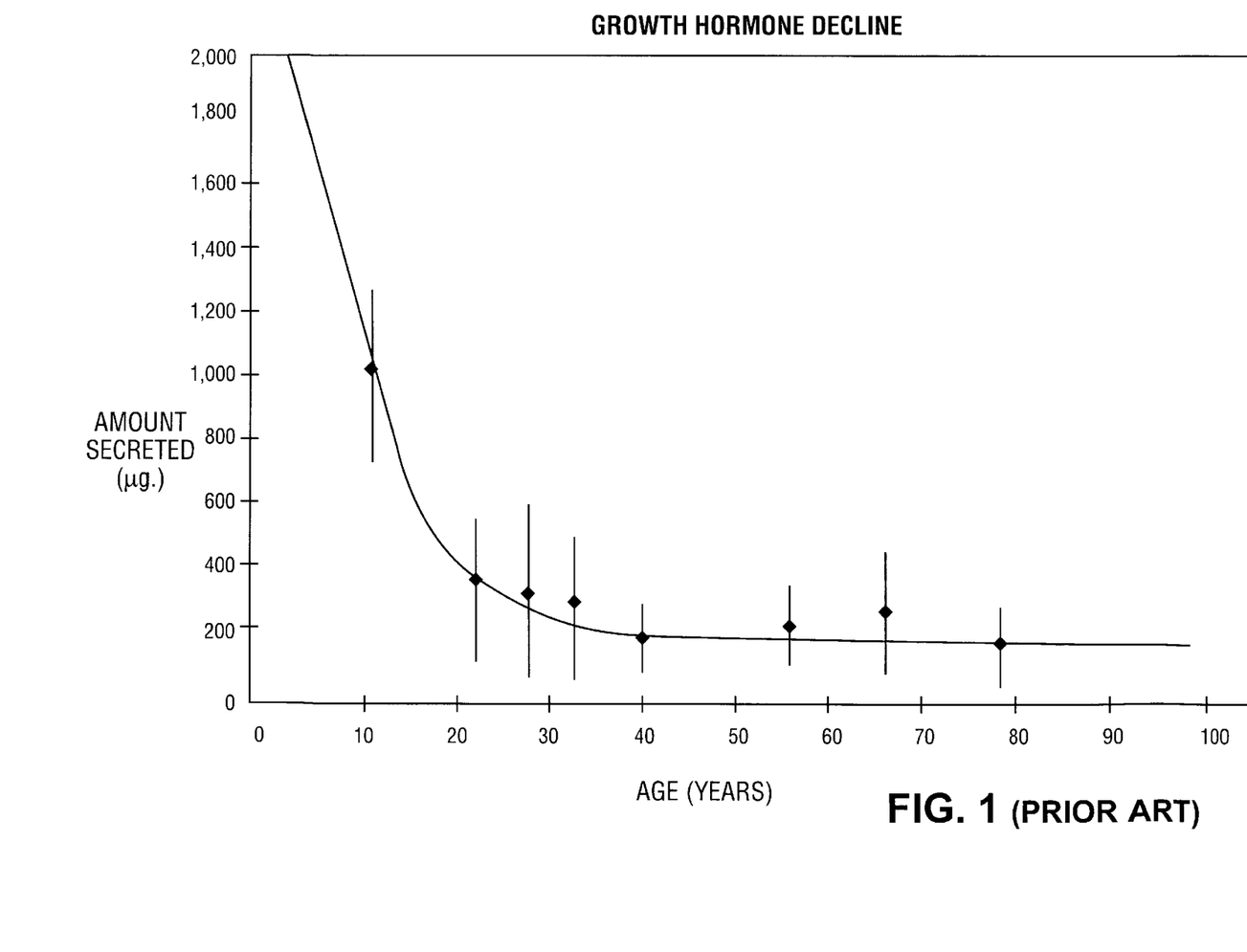
FIG. 1 illustrates the growth hormone decline in advancing years.

One of the hormones that declines sharply with age is human growth hormone (HGH, GH, or somatotropin). FIG. 1 illustrates the growth hormone decline in years for an ordinary human.

HGH is a protein hormone secreted by the somatotropic cells of the anterior lobe of the pituitary gland. HGH secretes in a pulsatile manner throughout a 24-hour period. The pulsatile diurnal output of growth hormone is modulated by a pair of inner synergistic hypothalamus hormones, the growth hormone releasing hormone (GHRH) and growth hormone inhibiting hormone (GHIH) or somatostatin. GHRH and GHIH are synthesized in the hypothalamus and transported along with other messenger hormones to the pituitary gland by means of a short specialized portal vein network. GHRH is essentially a series of short pulses, clocked at about once a minute uniformly throughout a 24-hour day. GHIH, on the other hand, is a "gatekeeper" that is normally abundant, but occasionally low, allowing pulses of growth hormone to be released from the pituitary gland into the bloodstream. The base line level of growth hormone, as far as serum concentration is concerned, is ordinarily at or below detectable limits from hour to hour.

The major secretion of HGH occurs at night, one to two hours after the onset of deep REM sleep. Peek secretion levels are between 10–50 ng/ml.

It is known that physiological roles are probably due both to direct actions of HGH and indirect actions mediated by the peptide hormones known as somatomedins. Somatomedins are stimulated predominantly by the action of HGH and include Insulin-like Growth Factor-I (also known as IGF-I and somatomedin-C) and IGF-II. The major site of somatomedin secretions is the liver, but there is also some production at peripheral sites.

Proper human growth from infancy is contingent upon adequate growth hormone secretion. Growth hormone appears to affect the growth of virtually every organ and tissue in the body. In normal development, HGH and the somatomedins are responsible for many manifestations of normal growth. Growth hormone deficiency during the childhood growing period is manifested by profound short stature. This deficiency has been treated by human growth hormone supplements for many years. However, the scarcity of the source material for natural HGH (i.e., pituitary glands of cadavers) has limited investigations into other possible applications for HGH. Recently, bioengineered HGH or recombinant HGH has been developed with identical characteristics as the natural HGH and removed the previous investigation limitations.

In 1990, a group of researchers published a report that showed that the declining activity of the IGF-I access with advancing age may contribute to the decrease in lean body mass and the increase of mass of adipose tissue that occur with aging. "Effects Of Human Growth Hormone In Men Over 60 Years Old", Rudman, D., M. D., et al., *The New England Journal of Medicine,* Vol. 323, No. 1, Jul. 5, 1990. Subsequent studies have shown that growth hormone increases bone mass in osteoporosis, reverses declining cardiac function, reverses declining pulmonary function, reverses the decline in immune function associated with aging, increases lean muscle mass, decreases the percentage of body fat, and increase the capacity for exercise. See Powrie, J. et al., "Growth Hormone Replacement Therapy For Growth Hormone-Deficient Adults", Drugs Vol. 49, No. 5, pages 656–63, 1995; Rosén, T., et al., "Consequences Of Growth Hormone Deficiency In Adults And The Benefits And Risks Of Recombinant Human Growth Hormone Treatment", Horm. Rees., Vol. 43, pages 93–99, 1995; and Hoffman, A. R., "Growth Hormone Therapy In The Elderly: Implications For The Aging Brain", Psychoneuroendocrinology, Vol. 17, No. 4, pages 327–33, 1992 (concluding that it is possible that chronic physiological GH and/or IGH-I replacement therapy might reverse or prevent some of the inevitable sequelae of aging).

Optimal or predetermined physiological levels for the hormones included in replenishment as an embodiment of the method of the invention are set forth in Table I. These levels are set based upon the average peak levels for the hormones which are present in adult humans at natural ages of optimal health, vigor and potency usually in the second and third decades of the average life span.

Figure 8:
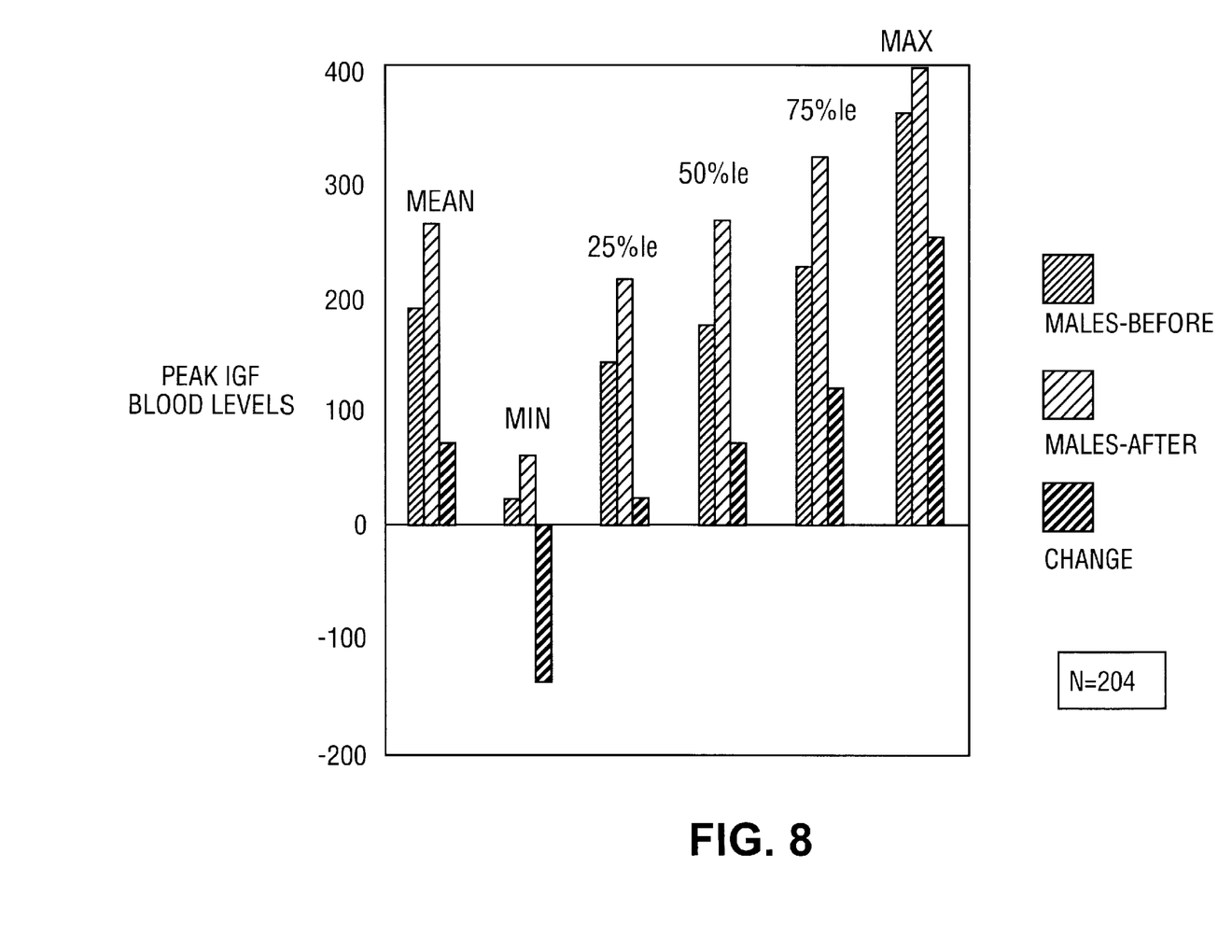
FIG. 8 presents the peak IGF-I levels in males before and after administration of IGF-I.
Figure 9:
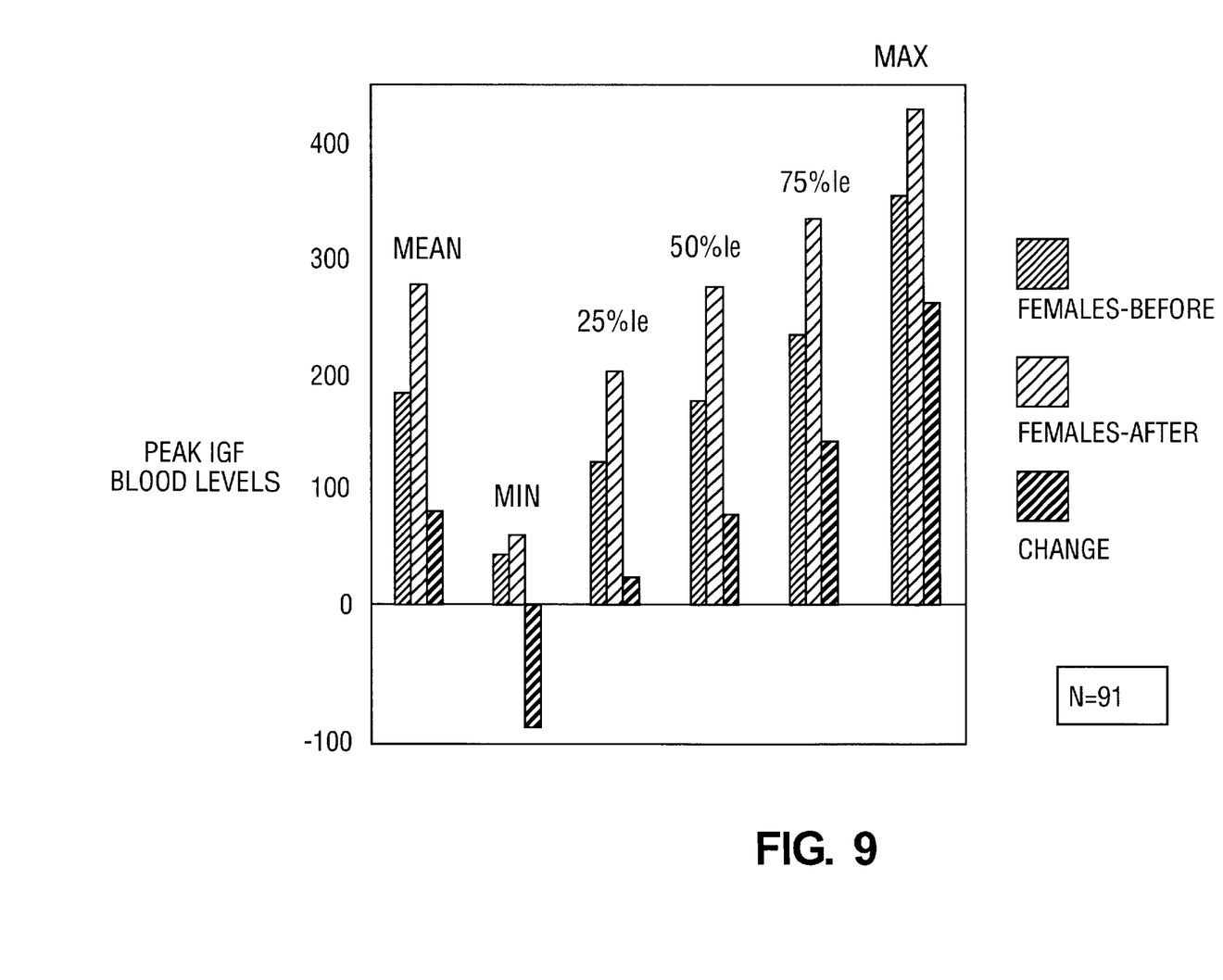
FIG. 9 presents the peak IGF-I levels in females before and after administration of IGF-I.

Table I shows that the HGH is measured by the level of IGF-I. Serum levels of HGH are difficult to measure. IGF-I is directly dependent upon the secretion of HGH by the pituitary gland, so therefore there is a direct linkage between increased secretion of HGH and increased production of IGF-I. Table II presents the effects of the low dose at high frequency human growth hormone administration (low dose-high frequency) contemplated by the invention on IGF-I (somatomedin C) blood levels. FIGS. 8 and 9 present the peak IGF-I levels in males and females, respectively, before and after administration of IGF-I. FIGS. 8 and 9 show mean, minimum and maximum, and 25, 50, and 75 percentile for 204 males and 91 females, respectively. Table III shows the data presented in FIG. 8. Table IV shows the data presented in FIG. 9.

TABLE I

| HORMONE | METHOD OF ADMINISTRATION | TARGET LEVEL (μg/ml blood) |
|---|---|---|
| HGH | injection | IGF-I = 350 |
| free testosterone | gel | female = 3, male = 40 |
| progesterone | capsule | 10–25 |
| estrogen | capsule | 100–200 |
| melatonin | capsule | 18–69 (at 3:00 am) |
| DHEA | capsule | female = 400, male = 600 |
| thyroid | tablet | T3 = 150–180 |
| pregnenolone | capsule | 100–200 |
| thymus hormone | Subligual powder | N/A |

TABLE II

Effects of Human Growth Hormone Administration (low dose-high frequency) on Somatomedin C Blood Levels
Somatomedin C. Blood Levels (mg/ml)

|  | Before hGH | After hGH | Increase |
|---|---|---|---|
| Mean | 238.8 | 384.5 | 61.0% |
| STDEV | 62.3 | 50.8 |  |
| SEM | 9.1 | 7.4 |  |
| No. Patients | 47.0 | 47.0 |  |
| MAX | 366.0 | 574.0 |  |
| MIN | 132.0 | 301.0 |  |

P < 0001

TABLE III

Males

| PEAK | IFG LEVELS | MALES BEFORE | MALES AFTER | MALES CHANGE | MALES DAYS |
|---|---|---|---|---|---|
| BEFORE | SAMPLE SIZE | MEAN | MEAN | MEAN | MEAN |
|  | 204 | 192.3 | 266.7 | 74.4 | 118.5 |
| AFTER | 204 | MEDIAN 183 | MEDIAN 272.5 | MEDIAN 75.5 | MEDIAN 82 |
|  |  | STDEV 61.7 | STDEV 75.1 | STDEV 73.2 | STDEV 110.3 |
|  |  | MIN 21 | MIN 63 | MIN −135 | MIN 6 |
|  |  | 25% ile 147 | 25% ile 217 | 25% ile 24 | 25% ile 40 |
|  |  | 50% ile 183 | 50% ile 273 | 50% ile 76 | 50% ile 82 |
|  |  | 75% ile 231 | 75% ile 325 | 75% ile 125 | 75% ile 146 |

TABLE III-continued

Males

| PEAK | IFG LEVELS | MALES BEFORE | MALES AFTER | MALES CHANGE | MALES DAYS |
|---|---|---|---|---|---|
| | | MAX 361 | MAX 396 | MAX 258 | MAX 639 |

TABLE IV

Females

| PEAK | IFG LEVELS | FEMALES BEFORE | FEMALES AFTER | FEMALES CHANGE | FEMALES DAYS |
|---|---|---|---|---|---|
| BEFORE | SAMPLE SIZE 91 | MEAN 162.2 | MEAN 236.3 | MEAN 74.0 | MEAN 133.4 |
| AFTER | 91 | MEDIAN 154 | MEDIAN 240 | MEDIAN 72 | MEDIAN 101 |
| | | STDEV 61.5 | STDEV 75.1 | STDEV 73.6 | STDEV 113.8 |
| | | SEM 6.4 | SEM 5.9 | SEM 4.8 | SEM 13.2 |
| | | MIN 41 | MIN 52 | MIN −93 | MIN 26 |
| | | 25% ile 111 | 25% ile 177 | 2.5% ile 26 | 25% ile 49 |
| | | 50% ile 164 | 50% ile 240 | 50% ile 72 | 50% ile 101 |
| | | 75% ile 205 | 75% ile 294 | 75% ile 128 | 75% ile 173 |
| | | MAX 311 | MAX 378 | MAX 231 | MAX 534 |

The method of determining the level of the select group of hormones may be accomplished by a simple blood test. A patients' blood is evaluated for the hormone levels of the select group of hormones and those levels are compared to the optimal or predetermined physiological levels set forth in Table I. Based on the comparison of a patient's hormone levels with the optimal or predetermined physiological levels, a regimen is established for the patient for the replenishment of the level of deficient hormones to optimal physiological levels. It is further contemplated, that after the initial evaluation and the establishment of the regimen, a patient is monitored every 30 days, by a similar blood test, until the patient attains the optimal or predetermined physiological level, and the dosages of hormone supplementation are adjusted accordingly. Once the target levels are established, the regimen directs that the patient continue to follow the established dosage of supplemental hormones indefinitely to maintain the optimal or predetermined physiological levels. Periodic blood tests are subsequently administered to assure that the optimal or predetermined physiological levels are maintained.

The optimal or predetermined physiological level of HGH and the supplemental hormones are set forth in Table I. These levels recognize the importance of each hormone to the body and are based on studies that indicate the period of life when the individual hormones are at their peak in the human body—generally in the second and third decade of an average human life span.

The method of the invention also contemplates that the HGH is administered in keeping with the way the pituitary secretes HGH naturally. The low dose-high frequency method mimics the pituitary gland. The pituitary secretes HGH 24 hours a day, with the peaks during the first two hours of sleep. The method contemplates that the patients take lower doses more frequently to try to mimic the natural rhythm of the body as much as possible. The invention contemplates that the patients take HGH injections at least twice daily. A preferred regimen calls for subcutaneous injections of doses less than 0.5 mg per day (approximately 1–3 I.U.), administered twice daily. Typical doses for this regimen range from 4 units per week to 8 units per week.

Because the invention contemplates that human growth hormone is administered in lower doses that mimic the natural rhythm of the body, the invention contemplates that the patient experiences none of the adverse side effects reported in earlier studies when higher pharmacological doses were given to patients more intermittently, e.g., 3 days per week.

Aside from the administration of HGH the invention contemplates therapeutic application of supplemental hormones. The supplemental hormones include the sex hormones, namely testosterone, progesterone, and estrogen, the melatonin hormone, the adrenal hormones, namely DHEA and pregnenolone, the thyroid hormone, and the thymus hormone. Dosage for administration of the supplemental hormones varies with the particular hormone.

Figure 2:
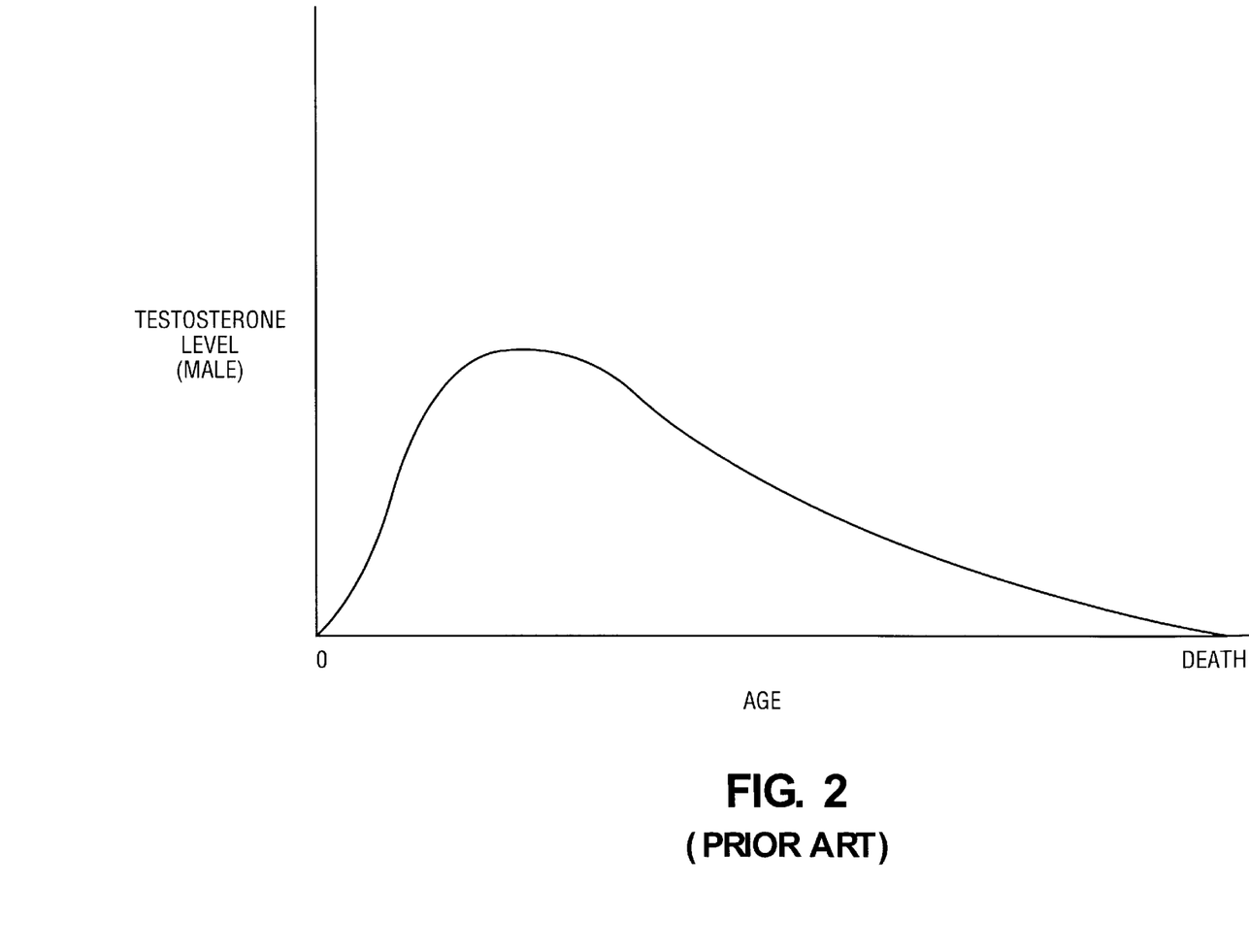
FIG. 2 illustrates the free testosterone levels in males throughout life.

The optimal or predetermined physiological level goal in testosterone replacement therapy in men is to maintain a total testosterone level at about 900–1200 μg/ml and a free testosterone level of about 30–40 μg/ml throughout one's lifetime. FIG. 2 illustrates the free testosterone level in males throughout life and shows the level decreasing with advancing age. In women, the levels of testosterone to maintain are much less, specifically women should maintain a free testosterone level of about 3 μg/ml.

Possible side effects which can occur during testosterone replacement include some weight gain due to accumulation of lean body mass, fluid retention, and among patients taking supraphysiologic doses of androgens: decreased testicular size, azoospermia, and acne.

Figure 3:
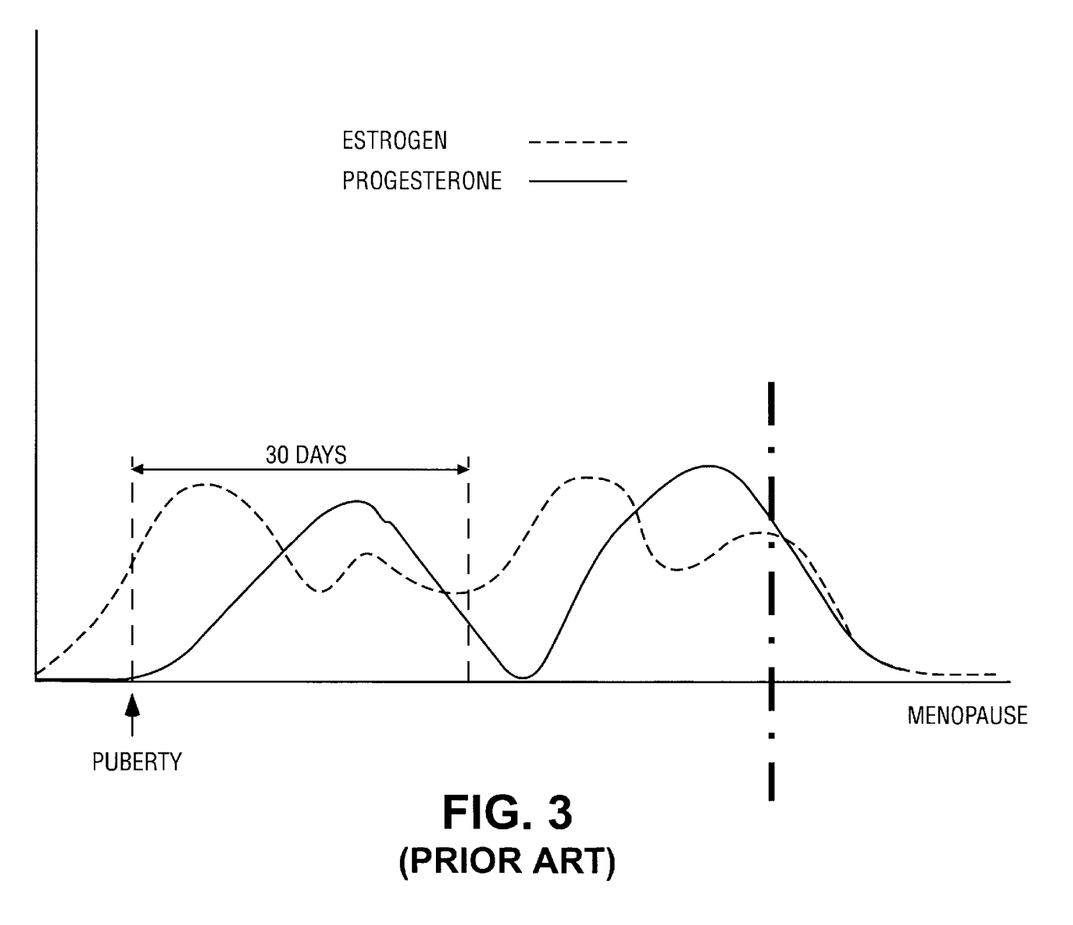
FIG. 3 illustrates the levels of estrogen and progesterone in females before and after menopause.

FIG. 3 illustrates the levels of estrogen and progesterone in females before and after menopause. As noted above, candidates for supplemental estrogen or progesterone should replenish these hormones concurrently to avoid the risk of side effects. These hormones may be taken in capsule form.

The optimal or predetermined target physiological level of progesterone is 10–25 μg/ml blood, and of estrogen is 100–200 μg/ml blood.

Figure 4:
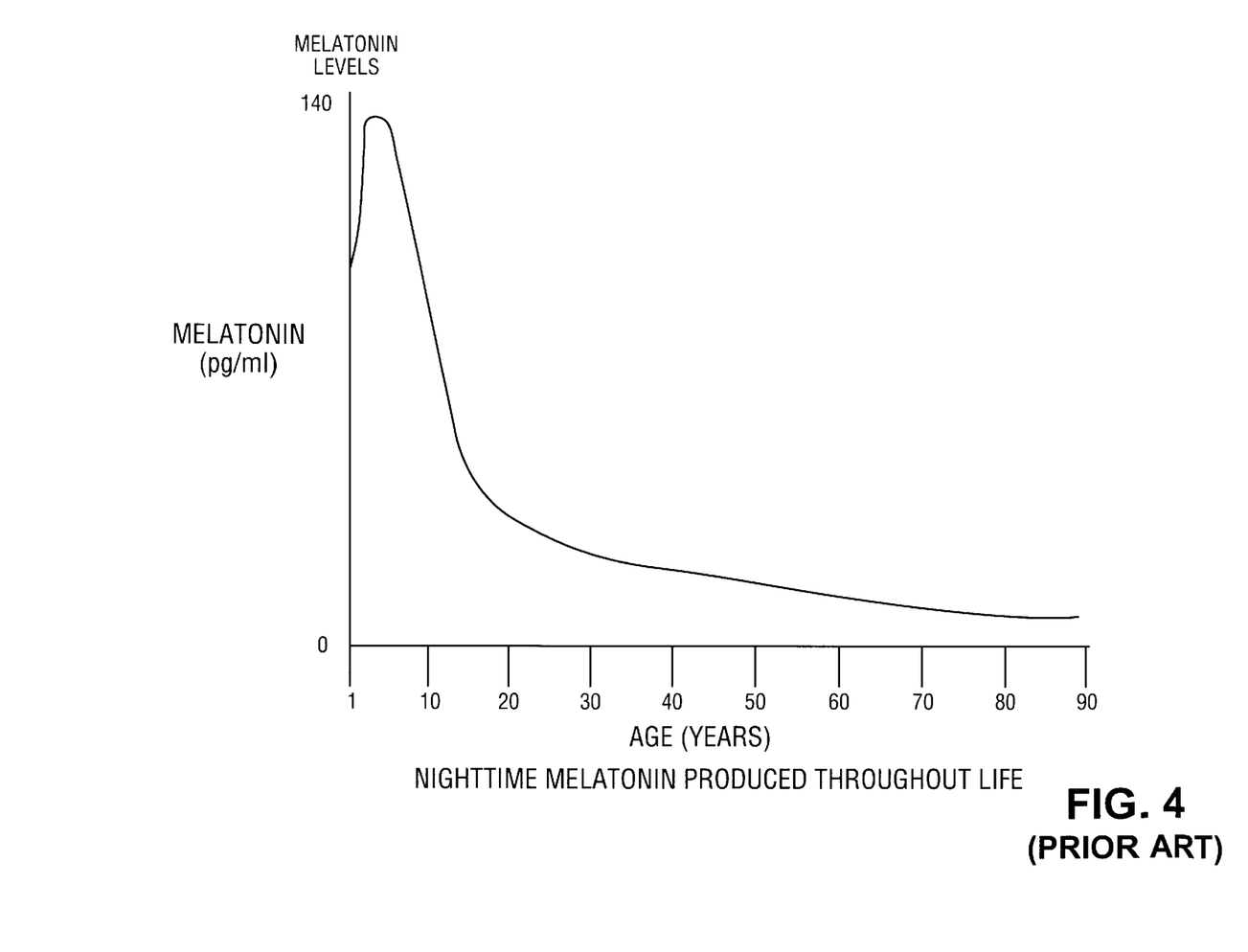
FIG. 4 illustrates the melatonin levels produced throughout life.

FIG. 4 illustrates the melatonin levels produced throughout life. The optimal or predetermined target physiological level of melatonin is 18–69 μg/ml determined by the average level of melatonin produced by a healthy young adult (i.e., 20–25 years). Further, melatonin supplementation has been shown to be completely harmless to the body and cause no side effects.

Figure 5:
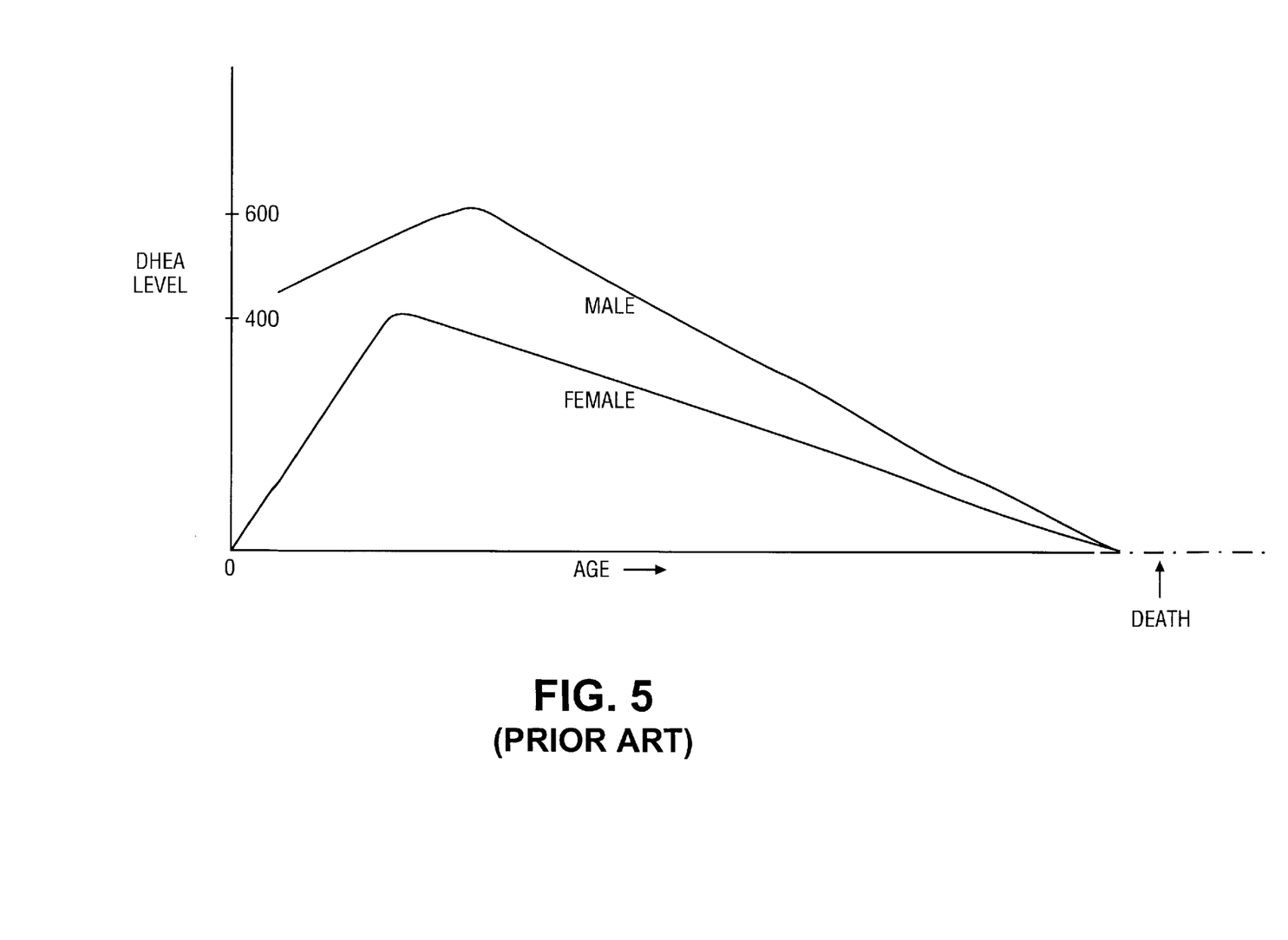
FIG. 5 illustrates the DHEA levels for males and females over a life span.

As noted above, the amount of the adrenal hormone DHEA peaks in the bloodstream of an individual at about 25 years of age. In one embodiment, FIG. 5 illustrates the DHEA levels for males and females over a typical life span. It is the peak physiological level that, in one embodiment, is the goal of the DHEA replenishment therapy. The optimal or predetermined physiological level of DHEA in a female is 400 μg/ml blood and in a male is 600 μg/ml blood.

The serum level of pregnenolone for normal adults ranges between 50 to 350 μg/ml of blood. If a person's level is low and falls outside of this range, replacement is recommended. Depending on the degree to which a patient may be deficient, the dose is approximately 100–200 milligrams ("mg") each day. The older or less healthy a person is, the more likely he or she will feel a dramatic effect from pregnenolone. A blood test is required to determine each individual's need for pregnenolone replacement, and to assess the proper dosage for therapy.

Figure 6:
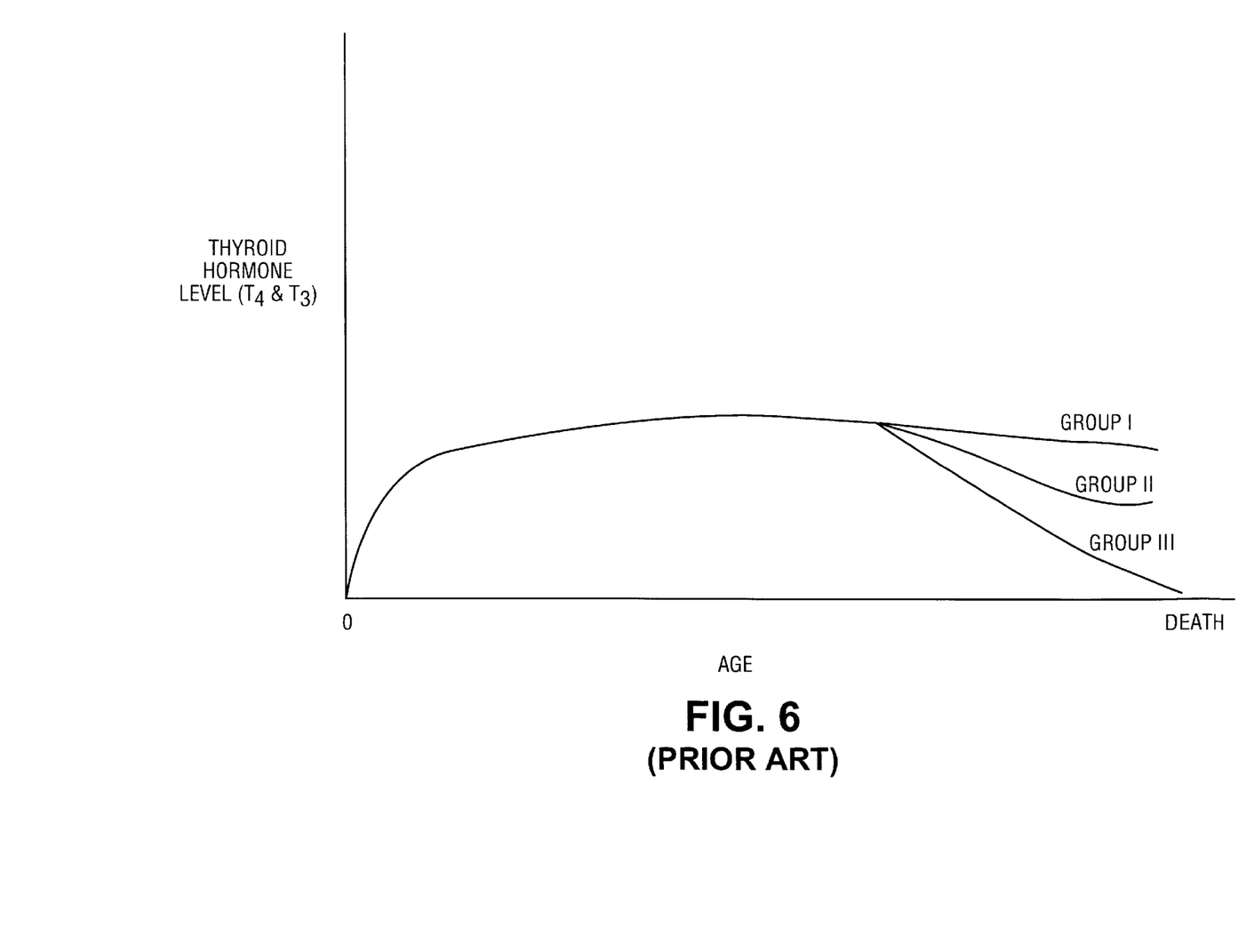
FIG. 6 illustrates the thyroid hormone levels versus age.

Maintaining sufficient thyroid hormone levels is also beneficial. FIG. 6 illustrates thyroid hormone levels versus age. Supplementation with thyroid hormone, particularly T-3 to 150–180 μg/ml of blood is contemplated by the invention.

Figure 7:
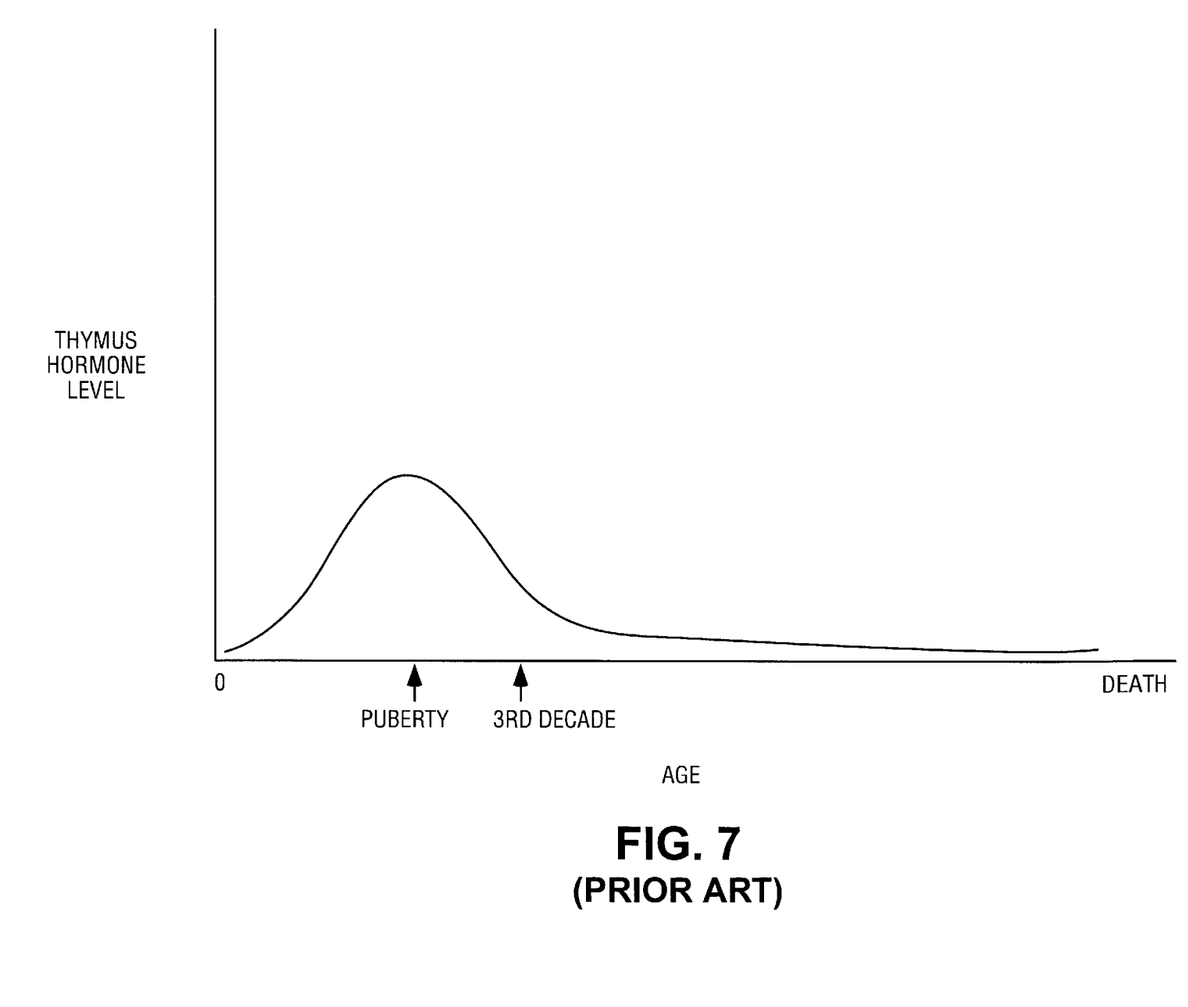
FIG. 7 illustrates the thymus hormone levels versus age.

FIG. 7 illustrates thymus hormone level versus age. Laboratory results indicate that the presence of thymus hormone in circulation can have an effect on a variety of other organ systems. All four thymic preparations (i.e., thymosin, thymulin, THF, and thymopoietin) are commercially available. Such a replacement therapy is totally harmless. The Food and Drug Administration has not regulated thymic hormones because they are not yet considered drugs or pharmaceuticals. Thymus hormone is in the same status and classification as DHEA and melatonin hormones which are also available over the counter.

By maintaining the optimal or predetermined physiological levels of human growth hormone and the supplemental hormones described above, the treatment is effective for reducing symptoms commonly associated with MS. As noted in the Background of the Invention section, diagnosis of MS is by exclusion, i.e., all other alternative diagnoses of a demyelinating condition must be ruled out before a diagnosis of MS may be established. The following case studies of patients with demyelinating conditions demonstrated from testing are illustrative of the effectiveness of the invention in patients with symptoms consistent with MS:

Case 1: (43 Year Old Male)

An MRI of the brain during the first exam in 1995 revealed multiple white matter signal abnormalities as well as subtle diffuse signal abnormalities consistent with MS. Soon after this test, the patient was placed on a hormone replenishment regimen, featuring twice daily subcutaneous doses of human growth hormone in the amount of 0.5 mg. per dose. Testosterone, melatonin, DHEA, thyroid, pregnenolone, and thymus hormone were also given in the manner previously described to optimal levels.

A later exam in 1998 noted significant diminishment of lesions, including the actual disappearance from the MRI scan of lesions. The examining physician noted that the previously noted large left middle cerebellar peduncle lesion was very subtle on the current film and was initially interpreted as normal. There was also a small lesion in the anterior limb of the internal capsule seen on the 1995 study which is not currently visualized. Finally, the examining physician noted that there was a right posterior frontal deep white matter lesion that was slightly smaller than previously noted in 1995 with the remaining lesions noted from the 1995 examination remaining essentially unchanged. Brain evoked response studies also indicate improvement in speed of neurotransmission after this treatment. For example, visual evoked responses may reveal optic nerve involvement by MS. Studies of the patient's visual evoked responses before and after hormone replenishment therapy revealed faster conduction speed after the therapy, indicating improvement in the optic nerve. The patient also regained complete motor strength and sensory disturbances disappeared.

Case 2: (Female 60 Years of Age)

Brain MRI scan taken in 1993 revealed multiple punctate foci of increased signal intensity on T2 weighted images in the corona radiata and basal ganglia and thalami, compatible with the presence of multiple lacunar infarcts (areas of necrotic tissue). The test also revealed lesions in the deep cerebral structures involving white matter and a lesion in the right side pons was observed to be approximately 1.0 cm in size. The conclusion by the examining physician was "thought extensive widespread infarcts could account for all the above described findings, the patient's age and sex makes this somewhat less likely and a demyeliting process, such as multiple sclerosis must be considered. Certainly this diagnosis could account for all the abnormal findings seen."

In January of 1995, with no observed changes in her condition, the patient initiated hormone replenishment treatment including subcutaneous injection twice daily of 0.5 mg Human Growth Hormone, as well as supplemental hormones such as progesterone, estrogen, DHEA, melatonin and pregnenolone in doses previously described.

In October 1995 a further brain MRI showed the pontine lesion to decrease in size to approximately 0.4 cm (surrounded by a crescentric margin of subtle enhancement). With respect to other white matter foci, none showed abnormal enhancement. The examining physician concluded that the degree of enhancement had subsided considerably, as had the size of the individual pontine lesion. She also fully regained her motor strength and recovered from sensory disturbances.

The above case histories indicate that hormone replenishment and supplementation is effective at reducing the symptoms associated with MS. HGH administration, given in a low dose, high frequency regimen is believed particularly to be effective at reducing the symptoms of MS.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method of reducing symptoms consistent with multiple sclerosis in a human subject comprising:
   administering to the human subject a regimen of doses of human growth hormone of less than 0.5 mg. per day.

2. The method of claim 1, wherein administering the regimen of human growth hormone comprises subcutaneously injecting of doses of human growth hormone.

3. The method of claim 1, wherein administering the regimen of human growth hormone comprises subcutaneously injecting doses of human growth hormone twice daily.

4. The method of claim 1, further comprising prior to administering the regimen of human growth hormone, measuring the level of human growth hormone in the human subject's blood to determine that the level of human growth hormone is below an average peak physiological level for an adult human, and replenishing the level of human growth hormone of the subject to the average peak physiological level for an adult human.

5. The method of claim 4, further comprising, in the human subject, measuring a level of a supplemental hormone selected from the group consisting of sex hormone, melatonin hormone, adrenal hormone, thyroid hormone and thymus hormone to determine that the level of the supplemental hormone is below an average peak physiological level for an adult human; and replenishing the level of supplemental hormone of the subject to the average peak physiological level of the adult human.

6. A method of reducing symptoms consistent with multiple sclerosis in a human subject comprising:

measuring a blood sample of the human subject to determine that the level of human growth hormone in the blood sample is below the average peak physiological level for an adult human; and replenishing the level of human growth hormone in the subject to the average peak physiological level for an adult human with doses of human growth hormone of less than 0.5 mg. per day.

7. The method of claim 6, wherein replenishing the level of human growth hormone comprises subcutaneously injecting doses of human growth hormone.

8. The method of claim 6, wherein replenishing the level of human growth hormone comprises subcutaneously injecting doses of human growth hormone twice daily.

9. The method of claim 6, further comprising measuring a level of a supplemental hormone in the human subject's blood, the supplemental hormone selected from the group consisting of sex hormone, melatonin hormone, adrenal hormone, thyroid hormone and thymus hormone to determine that at least one of the hormones is below the average peak physiological level for an adult human; and replenishing the level of the supplemental hormone of the subject to the average peak physiological level for an adult human.

* * * * *

UNITED STATES PATENT AND TRADEMARK OFFICE
CERTIFICATE OF CORRECTION

PATENT NO. : 6,187,750 B1  
DATED : February 13, 2001  
INVENTOR(S) : Chein

Page 1 of 1

It is certified that error appears in the above-identified patent and that said Letters Patent is hereby corrected as shown below:

<u>Title page,</u>  
Item [57], ABSTRACT,  
Line 1, please omit "treating".

Item [56], OTHER PUBLICATIONS,  
Line 5, please delete "O" after "Oxandrolene".

<u>Column 9,</u>  
Line 19, insert -- the -- after "the level of".

Signed and Sealed this

Nineteenth Day of February, 2002

Attest:

Attesting Officer

JAMES E. ROGAN  
*Director of the United States Patent and Trademark Office*